(12) United States Patent
Lebovic et al.

(10) Patent No.: US 8,705,689 B2
(45) Date of Patent: *Apr. 22, 2014

(54) DEVICE FOR CUSHIONING OF COMPRESSION SURFACES

(75) Inventors: Gail Lebovic, Palo Alto, CA (US);
George D. Hermann, Portola Valley, CA (US); David Willis, Palo Alto, CA (US);
Thomas A. Howell, Palo Alto, CA (US)

(73) Assignee: BioLucent, LLC, Bedford, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 13/351,149

(22) Filed: Jan. 16, 2012

(65) Prior Publication Data

US 2012/0114096 A1    May 10, 2012

Related U.S. Application Data

(63) Continuation of application No. 12/610,303, filed on Oct. 31, 2009, now Pat. No. 8,098,793, which is a continuation of application No. 10/946,044, filed on Sep. 21, 2004, now Pat. No. 7,616,732, which is a continuation of application No. 10/389,392, filed on Mar. 14, 2003, now Pat. No. 6,968,033, which is a continuation of application No. 09/620,730, filed on Jul. 20, 2000, now Pat. No. 6,577,702.

(60) Provisional application No. 60/187,198, filed on Mar. 6, 2000.

(51) Int. Cl.
*A61B 6/04* (2006.01)

(52) U.S. Cl.
USPC ................................ 378/37; 378/68; 378/208

(58) Field of Classification Search
USPC ........ 378/37, 68, 208; 600/407, 425; 128/915
See application file for complete search history.

(56) References Cited

U.S. PATENT DOCUMENTS

| 3,668,394 A | 6/1972 | Panzer |
| 3,963,933 A | 6/1976 | Henkes |

(Continued)

FOREIGN PATENT DOCUMENTS

| DE | 2335576 | 1/1975 |
| DE | 4324508 | 1/1995 |

(Continued)

OTHER PUBLICATIONS

Office Actions and translations (3) from Japanese Patent Office for corresponding JP Application No. 2001-564671, Applicant: BioLucent, LLC, Dated : Jun. 22, 2010, Nov. 24, 2010, and Apr. 19, 2011, 28 pages.

(Continued)

*Primary Examiner* — Jurie Yun
(74) *Attorney, Agent, or Firm* — William A. English; Vista IP Law Group LLP

(57) ABSTRACT

According to the present invention, improved methods and apparatus are provided for providing cushioning and other ergonomic surfaces on devices requiring the patient or tissue to be compressed, such as radiography machines, fluoroscopy units, mammography units and the like. In particular a radiolucent pad element is provided for releasable attachment to at least one surface of a compression device to be used under x-ray, for example, during mammography. The pad element of the present invention can be disposable or constructed to be reusable and in some cases may be applied directly to the patient's breast. Furthermore, a cushioned paddle is provided wherein the compression paddle and the cushion can be separately or integrally formed.

20 Claims, 14 Drawing Sheets

(56) References Cited

U.S. PATENT DOCUMENTS

| | | | |
|---|---|---|---|
| 4,030,719 | A | 6/1977 | Gabriele et al. |
| 4,346,298 | A | 8/1982 | Dixit |
| 4,433,690 | A | 2/1984 | Green |
| 4,923,187 | A | 5/1990 | Mombrinie |
| 4,943,986 | A | 7/1990 | Barbarisi |
| 5,044,008 | A | 8/1991 | Jackson |
| 5,081,357 | A | 1/1992 | Agano |
| 5,081,657 | A | 1/1992 | Klawitter |
| 5,161,273 | A | 11/1992 | Deck |
| 5,166,968 | A | 11/1992 | Morse |
| 5,189,686 | A | 2/1993 | Hixson |
| 5,226,070 | A | 7/1993 | Ariba |
| 5,377,254 | A | 12/1994 | Walling |
| 5,398,272 | A | 3/1995 | Bouscary |
| 5,416,822 | A | 5/1995 | Kunik |
| 5,474,072 | A | 12/1995 | Shmulewitz |
| 5,479,927 | A | 1/1996 | Shmulewitz |
| 5,541,972 | A | 7/1996 | Anthony |
| 5,553,111 | A | 9/1996 | Moore |
| 5,613,254 | A | 3/1997 | Clayman |
| 5,632,275 | A | 5/1997 | Browne |
| 5,657,367 | A | 8/1997 | Couch |
| 5,664,573 | A | 9/1997 | Shmulewitz |
| 5,719,916 | A | 2/1998 | Nelson |
| 5,754,997 | A | 5/1998 | Lussi |
| 5,832,550 | A | 11/1998 | Hauger |
| 5,891,074 | A | 4/1999 | Cesarczyk |
| 5,970,119 | A | 10/1999 | Hofmann |
| 6,049,583 | A | 4/2000 | Galkin |
| 6,577,702 | B1 * | 6/2003 | Lebovic et al. ............ 378/37 |
| 8,098,793 | B2 * | 1/2012 | Lebovic et al. ............ 378/37 |

FOREIGN PATENT DOCUMENTS

| | | |
|---|---|---|
| DE | 19926446 | 1/2000 |
| DE | 19921100 | 3/2000 |
| EP | 0682913 | 11/1995 |
| FR | 2702059 | 9/1994 |
| GB | 938410 | 6/1962 |
| JP | 349811 U | 5/1991 |
| JP | 03132273 | 6/1991 |
| JP | 04064346 | 2/1992 |
| JP | 05-078624 | 3/1993 |
| JP | 10-033526 | 2/1998 |
| WO | 9607353 | 3/1996 |
| WO | 9613211 | 5/1996 |

OTHER PUBLICATIONS

Office Actions and Responses from European Patent Office for corresponding EP Application No. 01914717.2-1526, Applicant: BioLucent, LLC, Dated from Jun. 6, 2003 to Sep. 26, 2011, 85 pages.
Office Actions and Responses from European Patent Office for corresponding EP Application No. 10181093.5, Applicant: BioLucent, LLC, Dated from Apr. 5, 2011 to Mar. 28, 2012, 31 pages.
GE Medical Systems, GE Accessories and Supplies for Diagnostic Imaging, Catalogue pages, Copyright 1995, vol. 5, General Electric, Milwaukee, Wisconsin, 3 pages.
GE Medical Systems, GE Accessories and Supplies for Diagnostic Imaging, Catalogue pages, Copyright 1997, vol. 6, General Electric, Milwaukee, Wisconsin, 4 pages.
GE Medical Systems, GE Accessories, Catalogue pages, 1997/98, Copyright 1997, General Electric, Milwaukee, Wisconsin, printed in France, 1997, 5 pages.
B. Galkin, The Breast Pillow TM: A Novel Device to Reduce Patient Disconfort and Pain During Mammography . . . , http://www.aapm.org/metting/01am/prabs.asp?mid=6&aid=7295, Jul. 2001, 2 pgs.
International Search Reports and Inernational Preliminary Examination Reports from WIPO for PCT/US01/07189, dated Sep. 17, 2001 and Jul. 10, 2002; and PCT/US02/23576, dated Mar. 14, 2002 and Mar. 3, 2003, 25 pgs.
S&S Par Scientific, VacFix Literature, HP002/0307, Houston, TX. Mar. 2002, 16 pages.
John K. McCulloch, Letter dated Dec. 7, 2005 with exhibits including tray liner, positioning aid literature, and 510(k) excerpt, 9 pages.
John K. McCulloch, Letter dated Dec. 9, 2005 with drawings of CFI Mammography Wdge, 3 pages.
Excerpts from BioLucent, Inc. 510(k) Notification including predicate device marketing literature, Dec. 6, 2000, 7 pages.
AAPM Report No. 29, Equipment Requirements and Quality Control for Mammography, Aug. 1990, For American Association of Physicists in Medicine, 79 pages.
Khalkhali, Iraj, Ismael Mena & Linda Diggles, Review of imaging techniques for the diagnosis of breast cancer . . . , European Journal of Nuclear Medicine, Apr. 1994, V. 21, No. 4, 6 pgs.
Cone Instruments web catalog page, Scintimammography Pad with 8 mil vinyl cover, Item No. NO033008, 2004 Cone Instruments, Inc., 1 pg.
Nuclear Medicine Instruments & Accessories catalogue 28, Pinestar Technology Inc., Scintimammography Pad Set, p. 85, www.pinestar.com, 2006, 2 pgs.
Contour Fabricators, Inc. Medical Solutions Catalog, pp. 1-25, 34, www.cfimedical.com, 2006, 28 pgs.
Muntz, E. Phillip & Wende Westinghouse Logan, Local Spot Size and Scatter Suppression . . . , AJR, Sep. 1979, vol. 133:453-459, American Roentgen Ray Society, 7 pgs.
ARRT 2005 Annual Report to Registered Technologists, The American Registry of Rediologic Technologists, St. Paul, Minnisota, 64 pages.
Wochos, John F., Gard D. Fullerton, & Larry A. DeWerd, Mailed Thermoluminescent Dosimeter Determination of Entrance Skin . . . , Am J Roentgnol 131:617-19, Oct. 1978, 3 pgs.
Pagani, John J., Lawrence W. Bassett, et al. Efficacy of Combined Film-Screen/Xeromammography, AJR, Jul. 1980, vol. 135:141-6, American Roentgen Ray Society, 6 pgs.
Parekh, N.J. & John N. Wolfe, localization Device for Occult Breast Lesions . . . , AJR, Apr. 1987, vol. 148:699-701, American Roentgen Ray Society, 3 pgs.
Robert L. Egan, M.D., Technologist Guide to Mammography, Second Edition, 1977, pp. 42-3 & 97, The Williams & Wilkins Company, Baltimore, Maryland, 7 pgs.
Wolfe, John N., Xeroadiography of the Breast, Second Edition, 1974, pp. 22 & 660, Charles C. Thomas publisher, Springfield, Illinois, USA, 4 pgs.
Lawrence Bigongiari, M.D., Barbara Threatt, et al., a Simple Device for Dependent Compression Mammography, Radiology, Aug. 1977, 124:516-17, Univ. of MI, Ann Arbor, Michigan, 3 pgs.
Lawrence Bigongiari, M.D., Barbara Threatt, et al., Dependent Compression Mammography, The Journal of Kansas Medical Society, Jun. 1979, vol. 80:336-40, Kansas City, Kansas, 6 pgs.
Howard Sochurek, Medicine's New Vision, 1988, p. 114, Mack Publishing Company, Easton, Pennsylvania, 3 pgs.
Daniel B. Kopans, M.D., Chapter 5: Mammography, Breast Imaging, 1989, pp. 34-59, J.B. Lippincott Company, Philadelphia, 30 pgs.
Bassett, Lawrence W. and Shirley Axelrod, A Modification of the Craniocaudal View in Mammography, Radiology, Jul. 1979, pp. 222-224, vol. 132 No. 1, The Radiological Society of North America, 4 pgs.

* cited by examiner

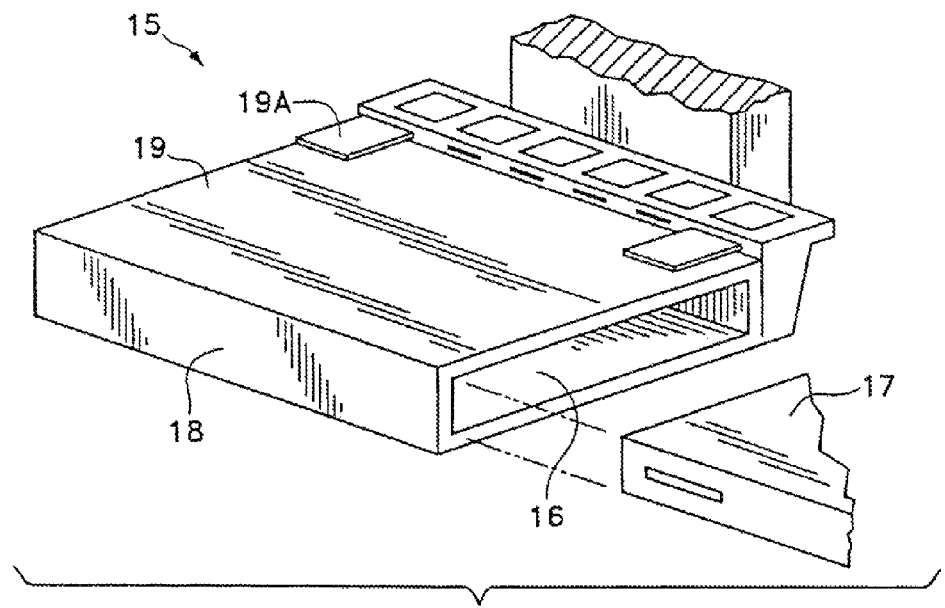
FIG. 2A
PRIOR ART
FIG. 2B
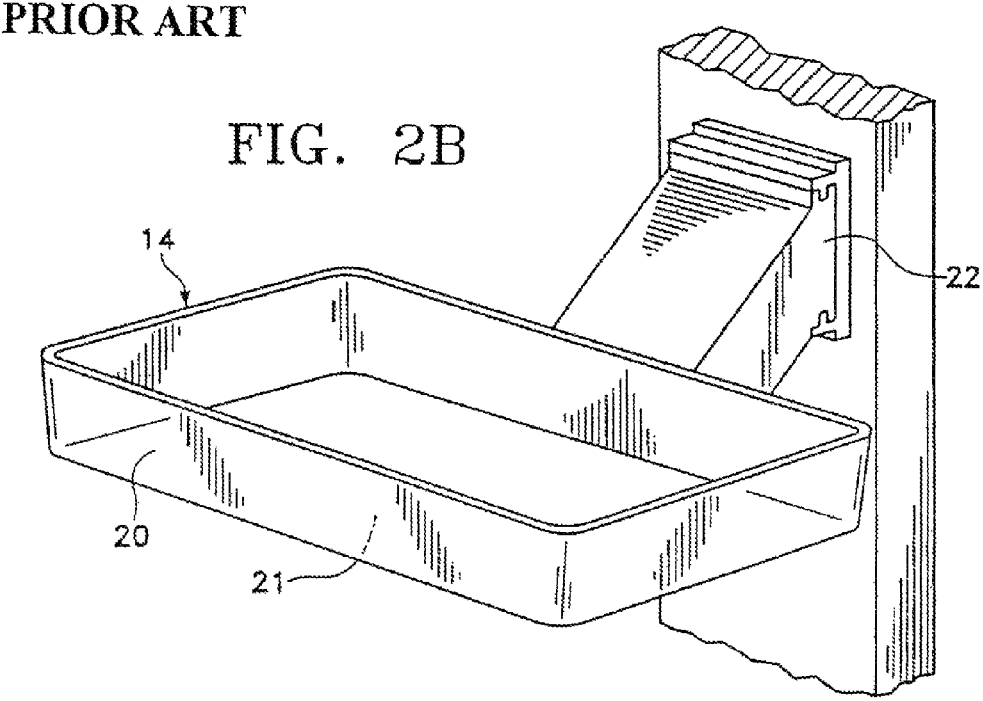

PRIOR ART

DEVICE FOR CUSHIONING OF COMPRESSION SURFACES

RELATED APPLICATION DATA

This application is a continuation of co-pending application Ser. No. 12/610,303, filed Oct. 31, 2009, issuing as U.S. Pat. No. 8,098,793 on Jan. 17, 2012, which is a continuation of Ser. No. 10/946,044, filed Sep. 21, 2004, now U.S. Pat. No. 7,616,732, which is a continuation of application Ser. No. 10/389,392, filed Mar. 14, 2003, now U.S. Pat. No. 6,968,033, which is a continuation of application Ser. No. 09/620,730, filed Jul. 20, 2000, now U.S. Pat. No. 6,577,702, which claims benefit of provisional application Ser. No. 60/187,198, filed Mar. 6, 2000.

BACKGROUND OF THE INVENTION

The present invention relates generally to medical apparatus and methods and more particularly to devices and methods for cushioning or padding the surface of compression plates applied to body parts for purposes of obtaining x-ray films for example mammography, or other scans of compressed tissue.

Currently, in the case of mammography, a patient's breast is placed under compression by opposing plates attached to a mammography machine. Once under compression an x-ray is taken to determine the presence or absence of suspect lesions in the breast tissue (e.g. calcifications, tumors). Approximately 25 million screening mammograms are performed yearly, which is estimated to be only a 50% compliance rate among potential patients, meaning that number would double if more patients complied with the recommended screening regime. One of the more common complaints from mammography patients is discomfort during compression of the breast. Most patients can only tolerate up to 10-11 compression units. The current legal limit for clinical mammography is 16-18 units. A device which would reduce discomfort could likely improve compliance for screening.

An important reason for compressing the breast during mammography is to provide a thinner cross section of tissue for the x-rays to pass through. When the breast is compressed, it provides optimal imaging of the tissue abnormalities with the lowest possible dose of x-ray radiation to the patient. Furthermore, during a mammogram, it is important for the x-ray plate to be free from radiopaque material, so that the diagnostic film, once processed, can give the physician the best possible picture of the tissue and any abnormalities.

Although patients may tolerate the pain during compression, there is a need for improved devices and techniques to provide better screening outcomes by enabling the use of higher compression force, and by providing increased patient comfort during mammograms thereby positively impacting patient compliance with mammographic screening and ultimately impacting early detection of cancer and improving patient survival.

Such improved devices must be radiolucent and made of a relatively homogeneous material to avoid striations or other variations on the resulting x-ray image, have a low profile to allow for correct positioning of the breast in the mammography machine, be easily cleaned or disposable for sanitary reasons, and provide structural support and tactile comfort to the patient (both soft to touch and providing a less harsh or "cold" surface). In addition, such improved devices will permit the use of higher compression forces to be applied to the breast during mammograms without the patient reaching her tolerance level for discomfort, resulting in a thinner tissue section, better image quality, and reduced x-ray dose to the patient.

It is an objective of the present invention to provide greater patient comfort thereby increasing screening compliance (e.g. patient willingness to have more regular mammograms by reducing discomfort of the procedure). Greater patient comfort also reduces the risk of patient movement (voluntary or involuntary). Motion artifact, caused by patient movement or slippage of the tissue, can result in loss of clarity of the mammographic image. It is a further objective of the present invention to allow for the use of an increased compressive force, for example, up to 16-18 compression units or more thereby providing for a thinner cross-section of breast tissue during the mammogram resulting in an enhanced ability to detect abnormalities in the mammographic image. These objectives are met by the design and use of the present invention.

DESCRIPTION OF THE BACKGROUND ART

Various patents have issued illustrating inventions in the field of mammography and comfort during x-ray imaging. For example, in the field of mammography, U.S. Pat. Nos. 3,963,933, 4,691,333, 4,943,986, 5,189,686, 5,553,111 and 5,398,272 describe various fixtures useful for breast compression. Further, patents have issued describing devices for increasing comfort during general x-ray procedures, such as U.S. Pat. No. 5,226,070 (radiolucent x-ray mat), U.S. Pat. No. 5,081,657 (bucky warmer for mammography machine), U.S. Pat. No. 5,541,972 (disposable padding device for use during mammography), and U.S. Pat. No. 5,185,776 (padded cover for x-ray cassette).

SUMMARY OF THE INVENTION

According to the present invention, improved methods and apparatus are provided for cushioning or providing other patient comfort surfaces on devices used for compressing the patient's tissue, such as radiography machines, fluoroscopy units, mammography units and the like. In particular a pad element is provided for releasable attachment to at least one surface of a compression device to be used under x-ray, or other imaging modality.

In a preferred embodiment of the present invention a pad assembly is provided consisting of a pad element, an adhesive layer and a release paper layer allowing for temporary attachment to the applied surface (either the mammography paddle, x-ray plate or directly to the patient's skin).

An alternative embodiment of the present invention includes a reusable cushioned paddle configured of a self-skinned foam to allow for easy cleaning between patients. This embodiment may be replaceable after many uses or formed integrally wherein the padded surface and the compression paddle are assembled as one unit.

The present invention may also incorporate a dispensing unit for access to single pads for single use.

BRIEF DESCRIPTION OF THE DRAWINGS

FIGS. 2A-2B illustrate detailed construction of the x-ray plate and the compression paddle respectively.

DETAILED DESCRIPTION OF THE PREFERRED EMBODIMENTS

Figure 1:
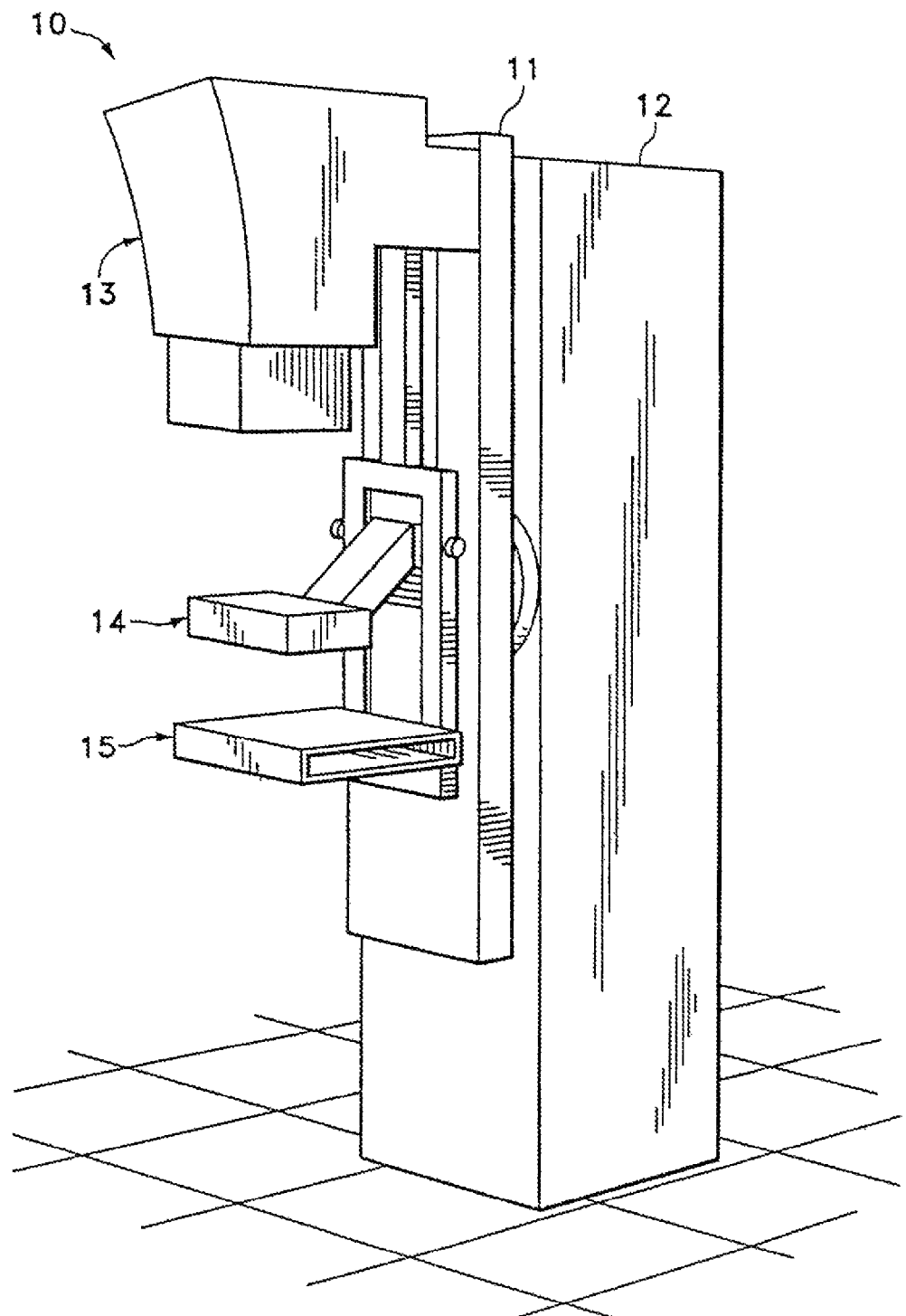
FIG. 1 illustrates a typical mammography unit having a base and a pivoting x-ray unit attached thereto, the x-ray unit including a compression paddle and an x-ray plate.

A typical or standard mammography unit used to image the breast while under compression is shown in FIG. 1. This unit 10 includes a base 12 and a rotating x-ray source 11, comprising an x-ray source 13, a movable compression paddle 14 and an x-ray plate 15 that holds the film cassette (not shown) as well as serving as a compression surface against which the compression paddle 14 can compress tissue, e.g., a breast to be imaged. As depicted in FIG. 2A, typically the x-ray plate 15, in certain configurations known as a "bucky," is stationary and includes an opening 16 into which an x-ray cassette 17 is placed prior to imaging. The x-ray plate has two patient contact surfaces, a front face 18, and a functional surface 19. The x-ray plate 15, may optionally include radiopaque markers 19A at the perimeter of the functional surface 19 to allow various marking schemes to be utilized during a procedure.

Figure 3A:
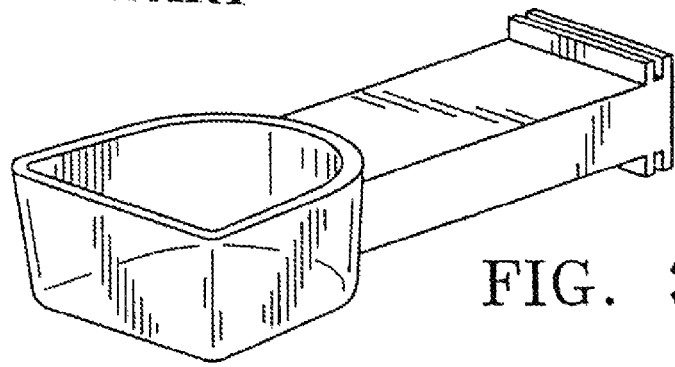
FIGS. 3A-3C illustrate various configurations of compression paddles utilized during mammography in a standard mammography machine; the shape and size depending both on the patient's anatomy and the type of x-ray view desired by the physician.
Figure 3B:
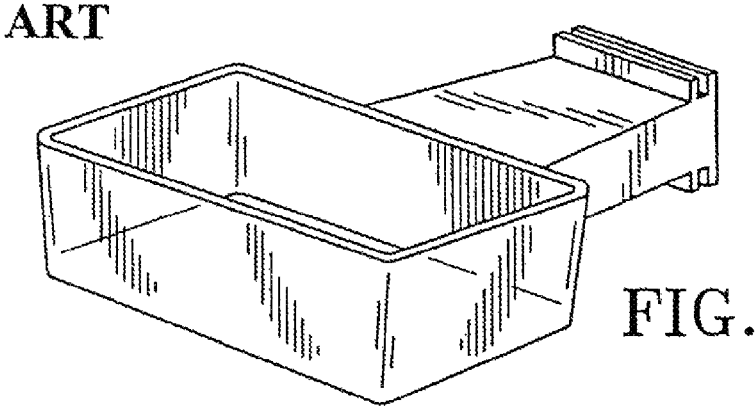
Figure 3C:
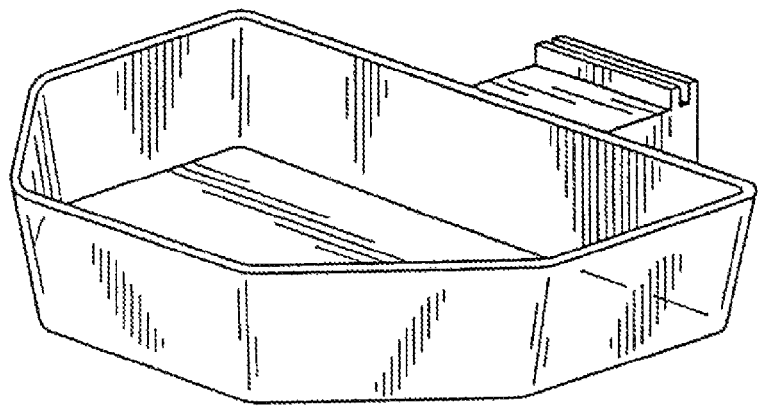

FIG. 2B illustrates a more detailed configuration of compression paddle 14, including a front patient contact surface 20 and a functional patient contact surface 21. Paddle 14 is typically constructed of a clear radiolucent plastic material and is designed to be removably attached by an interchange assembly 22, to the movable working arm of the mammography machine (not shown). These paddles are configured in various geometries as depicted in FIGS. 3A-3C to accommodate various patient anatomies and specific needs of mammographers, such as coned compression paddles (3A), spot compression paddles (3B) and the axillary paddle shown as FIG. 3C, all configured to attach to the mammography unit through standard interchange assembly 22, as shown earlier.

Figure 4A:
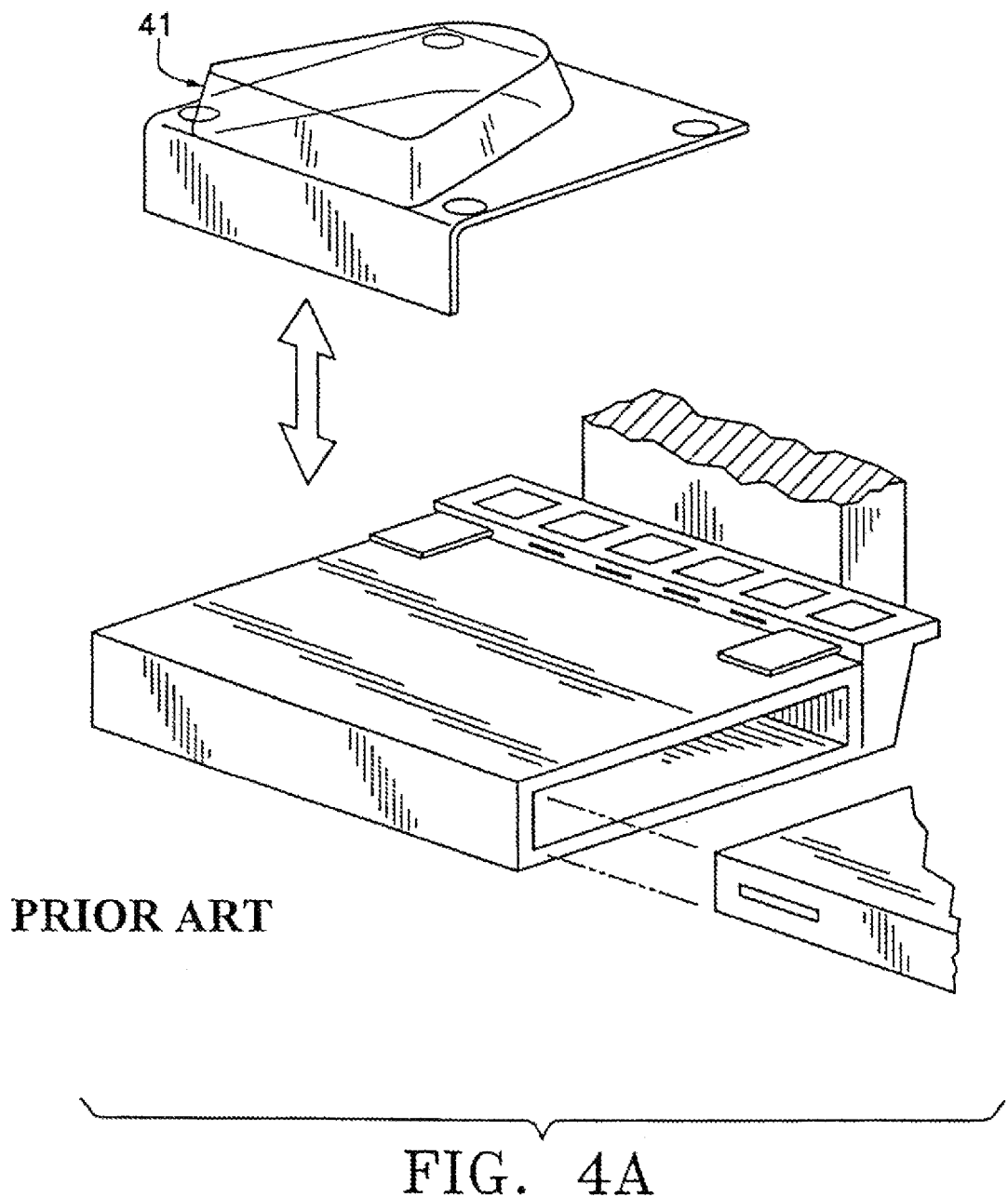
FIGS. 4A-4B illustrate various attachments that can be placed on the x-ray plate to enhance the image, including devices for spot compression and magnification.
Figure 4B:
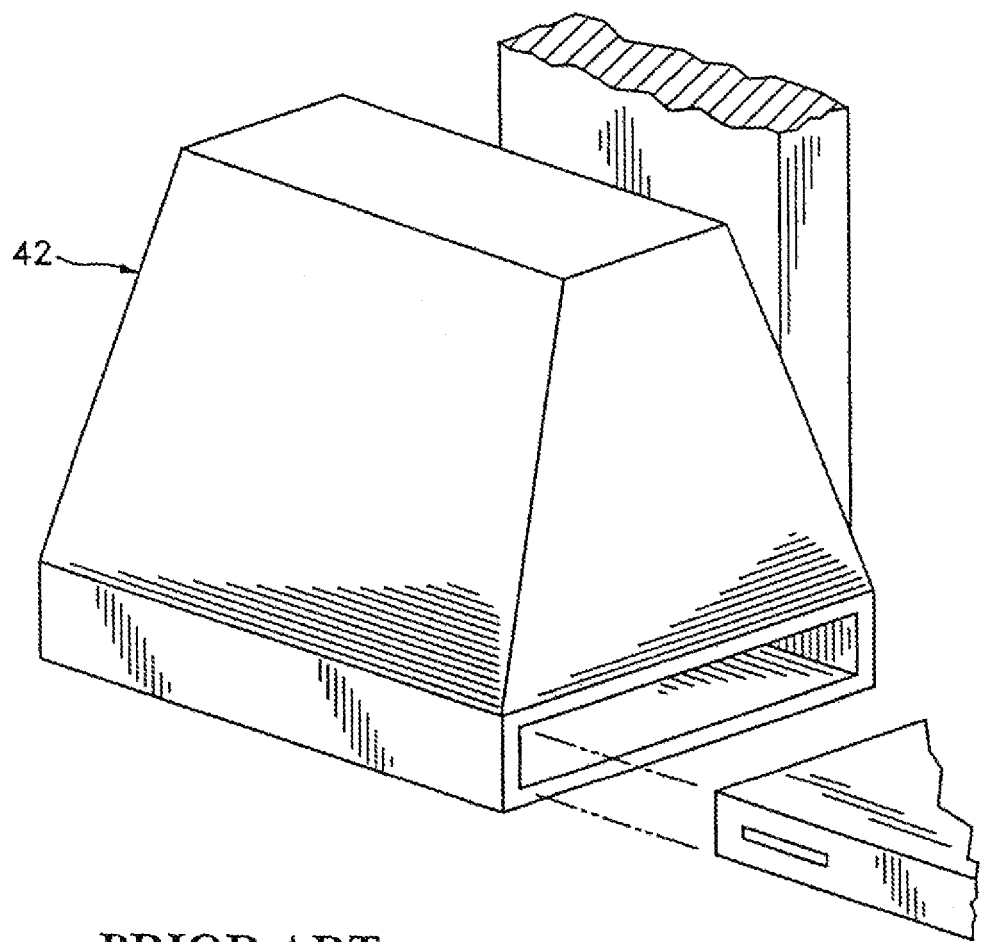
Figure 5:
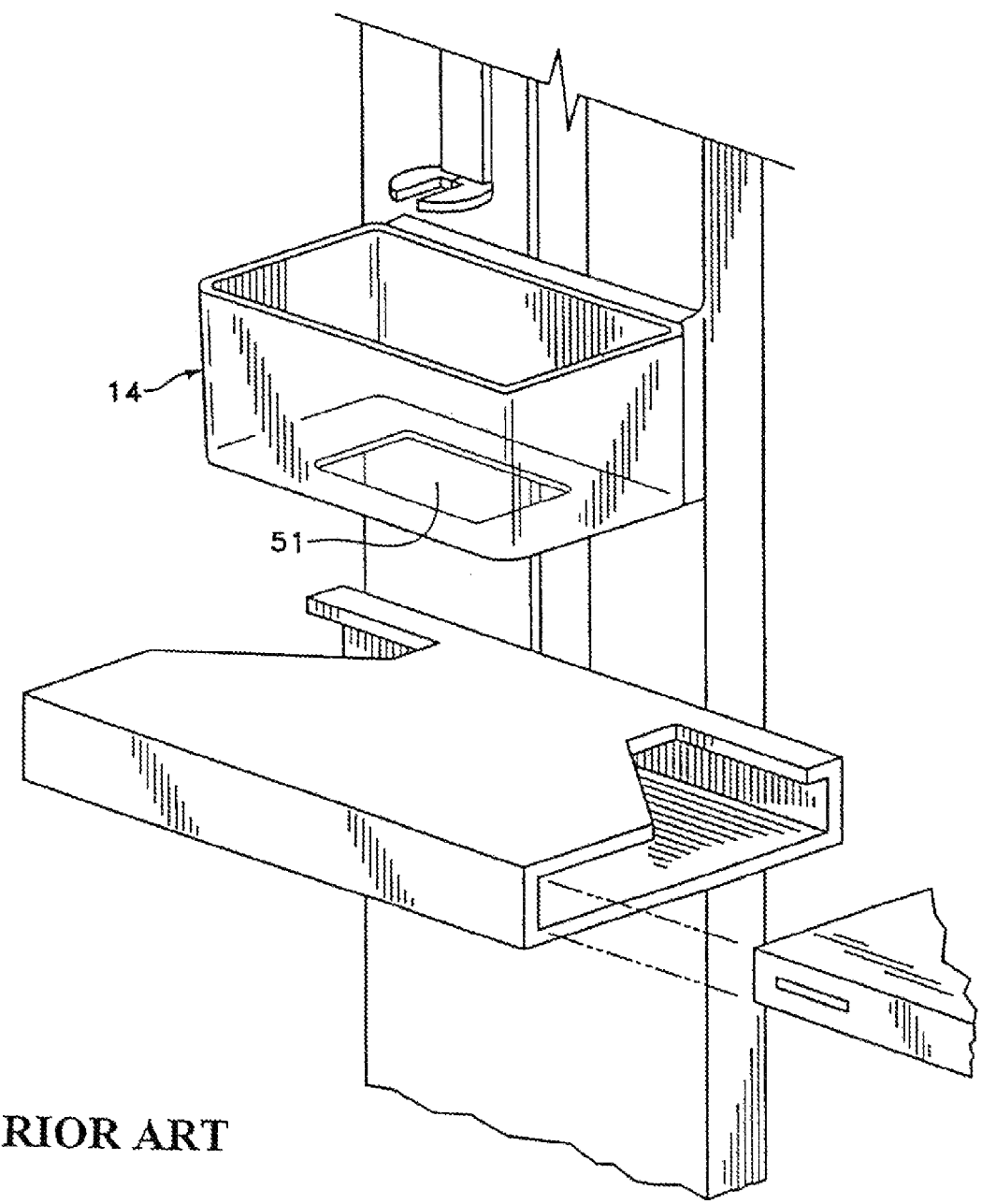
FIG. 5 illustrates a compression paddle and x-ray plate configured for use in a stereotactic biopsy procedure.

Similarly, the x-ray cassette holder may be adapted by various ancillary modules such as the spot compression fitting 41 shown in FIG. 4A, and a magnification fitting 42 shown in FIG. 4B. The entire compression system (compression paddle and x-ray plate) can further be modified to accommodate a stereotactic biopsy procedure as illustrated in FIG. 5. In this configuration, compression paddle 14, is modified to include a window 51, allowing the clinician access to the breast, while still under compression, for purposes of placing a device to identify a specific location in the breast, or to perform an biopsy of tissue.

Figure 6A:
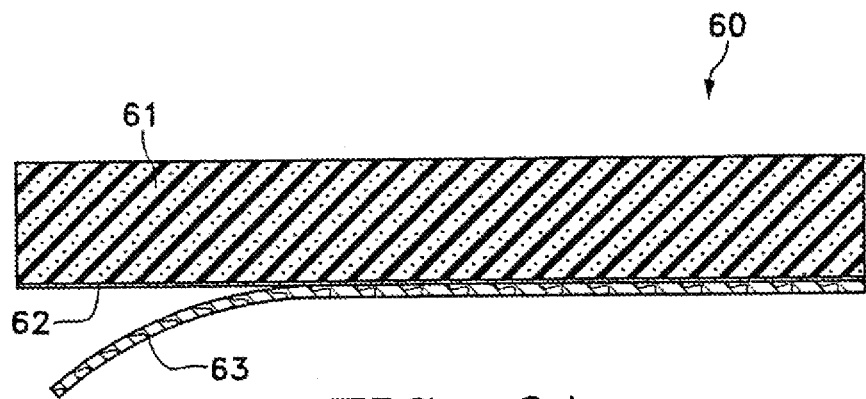
FIG. 6A illustrates the pad of the present invention having a padding layer, an adhesive layer and a release paper layer.

A preferred embodiment of a pad assembly constructed in accordance with the present invention is illustrated in FIG. 6A. The pad assembly 60 comprises a padding element 61, an adhesive layer 62, and a release paper 63 to be removed from contact with the adhesive layer just prior to installation on the surface to be padded. Pad element 61 may be constructed of various materials having the following characteristics: produce no significant visual artifact on the mammogram (i.e. is radiolucent), be deformable under the forces applied during compression to provide comfort. Furthermore, the material should provide conformance to the tissue and the compression surface so as to reduce the propensity for the material to create air pockets or folds that may be of sufficient size to be visible on the x-ray image. Additionally, it may be desirable for the material to be absorptive to external fluids such as sweat.

Such materials may be an elastomer or gel, open or closed cell foam consisting of polyolefin, or, preferably a hydrophilic polyurethane open cell foam because of its radiolucent characteristics and soft tactile feel. The padding material 61 may be a thickness of 0.050 inch to 0.500 inch, preferably in the range of 0.200 inch and 0.250 inch. If an adhesive layer is used, adhesive layer 62 may be one of a variety of currently available pressure sensitive adhesives such as acrylic or synthetic rubber based adhesives, to allow sufficient tackiness for secure attachment to the compression surface, while also allowing for easy removal (e.g., leaving no detectable residue of adhesive on the applied surface) and disposal. Alternatively, a non-adhesive gel may be used to secure the pad or another layer of material having a greater coefficient of friction against the applied surface. It is also anticipated by the scope of the present invention, that the pad element may itself be textured such that it is sufficiently "tacky" to enable its use without an adhesive layer, i.e., by means of friction between the element and the tissue and the unit compression surface.

Figure 6B:
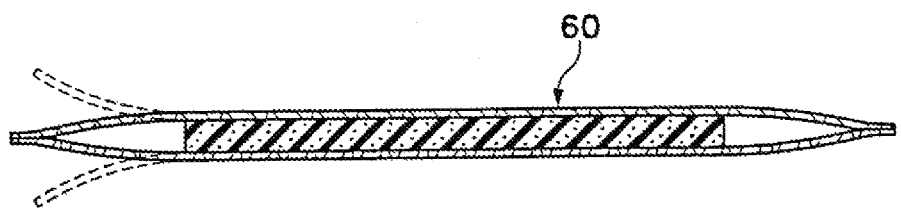
FIG. 6B illustrates another pad of the present invention within a "peel away" packet.
Figure 6C:
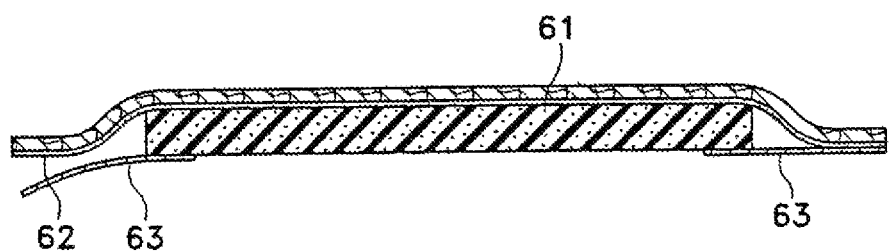
FIG. 6C illustrates still another pad of the present invention with an adhesive layer and release paper layer just along the border.

The pad element of FIG. 6A can be configured with adhesive on the entire surface of the pad, or at certain regions such as just along the border (see FIG. 6C). FIG. 6B depicts a "peel away" packet configuration to house the pad assembly. Optionally, the peel away packet can serve as a stiffening element to aid installation of the pad by keeping it in a planar configuration to minimize the possibility of misapplying the pad (leading to inadvertent air pockets or folds in the material, etc.) and to aid in positioning the pad prior to adhering it to the applied surface.

Figure 7:
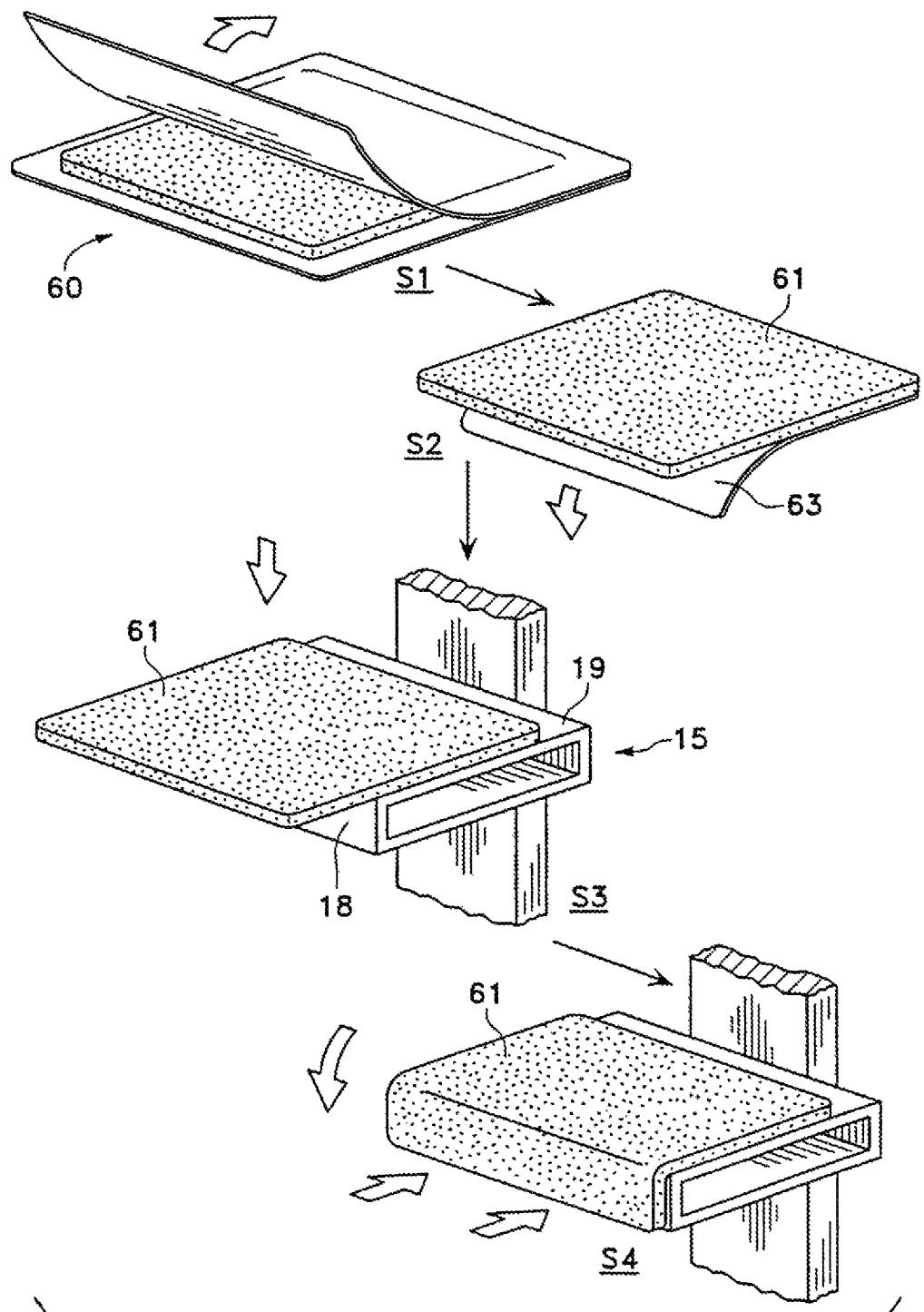
FIG. 7 illustrates the installation of the pad of the present invention on an x-ray plate.

FIG. 7 illustrates, in stepwise fashion, the installation of the pad assembly 60 of the present invention onto the film holder 15. The first step comprises opening the packing material housing the pad assembly 60 (S1), and thereafter removing any release paper 63 therefrom (S2). Installation on the patient contact surfaces of the x-ray plate 15 are shown in steps S3 and S4, S3 showing the placement of the pad element 61 on functional surface 19, and optionally extending to front face surface 18. Finally, the pad element may be removed and disposed of and the sequence repeated for the next patient. It may be desirable to score or otherwise provide a fold in the pad element at a fixed point from the edge of the pad to accommodate folding the pad onto the front face of the applied surface.

Figure 8:
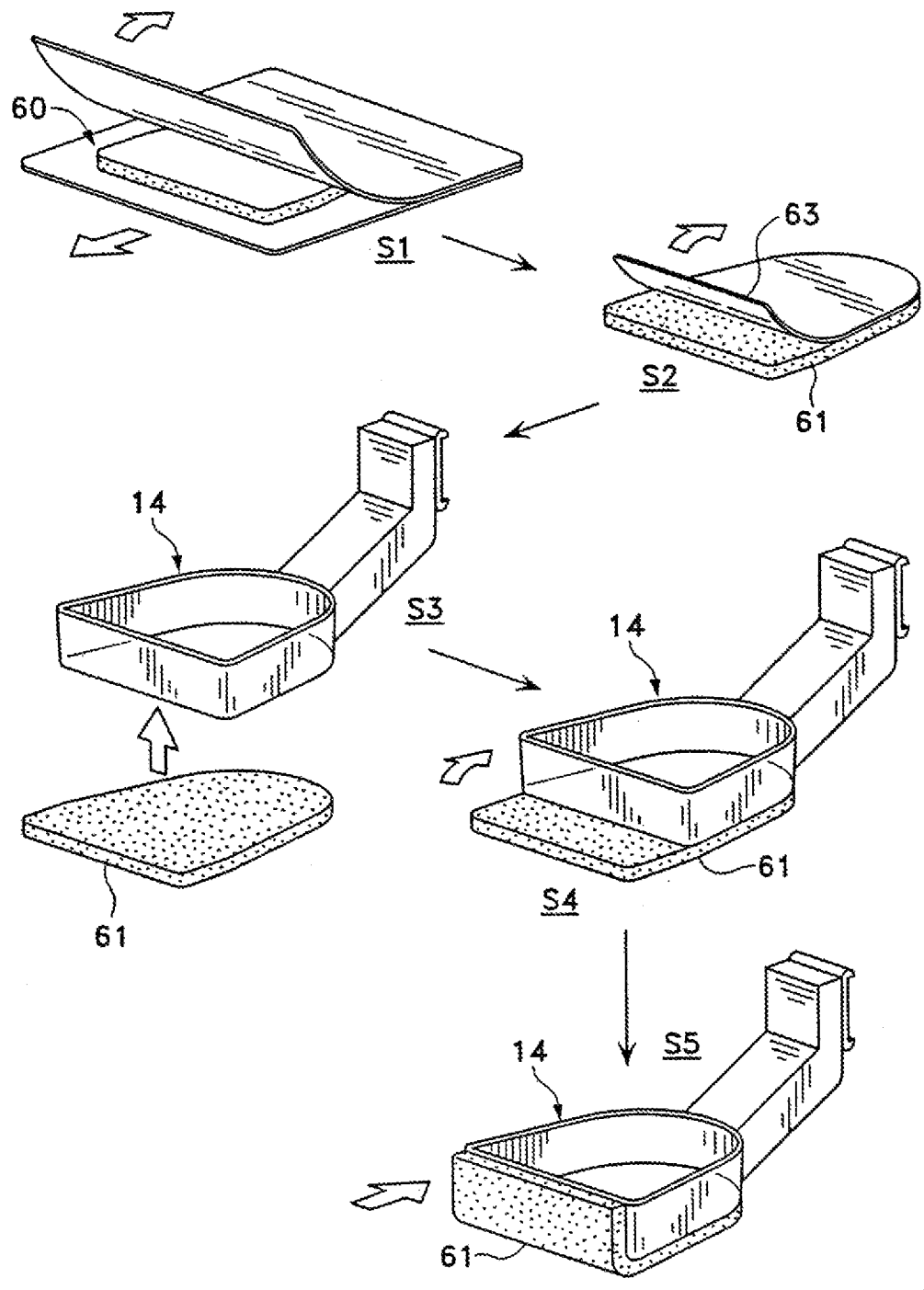
FIG. 8 illustrates the installation of the pad of the present invention on a compression paddle.
Figure 12:
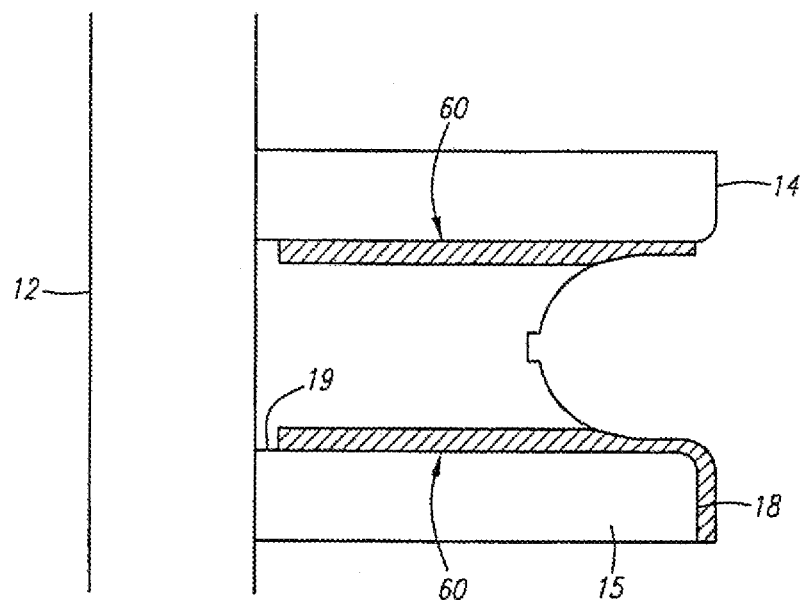
FIG. 12 shows a pad assembly on a film holder and compression plate, and a breast being compressed therebetween.

A similar sequence of steps (S1 to S4) is illustrated in FIG. 8 showing the installation of pad assembly 60 of the present invention onto compression paddle 14. It should be noted that the pad of the present invention may be installed on the x-ray plate 15 and the compression paddle 14, as shown in FIG. 12, or one and not the other, and further optionally on the front face of either surface depending on the amount of additional cushioning desired. In experimentation with the present invention, increased comfort was noted in all of the various configurations as compared to unpadded compression surfaces.

An alternative technique for use of the pad is to attach it to the breast of the patient instead of on the mammography machine itself. In this technique (not shown) the release paper is removed and the adhesive side of the pad is placed directly on the breast in an area of tissue to be compressed prior to placing the breast into the mammography machine.

Figure 9:
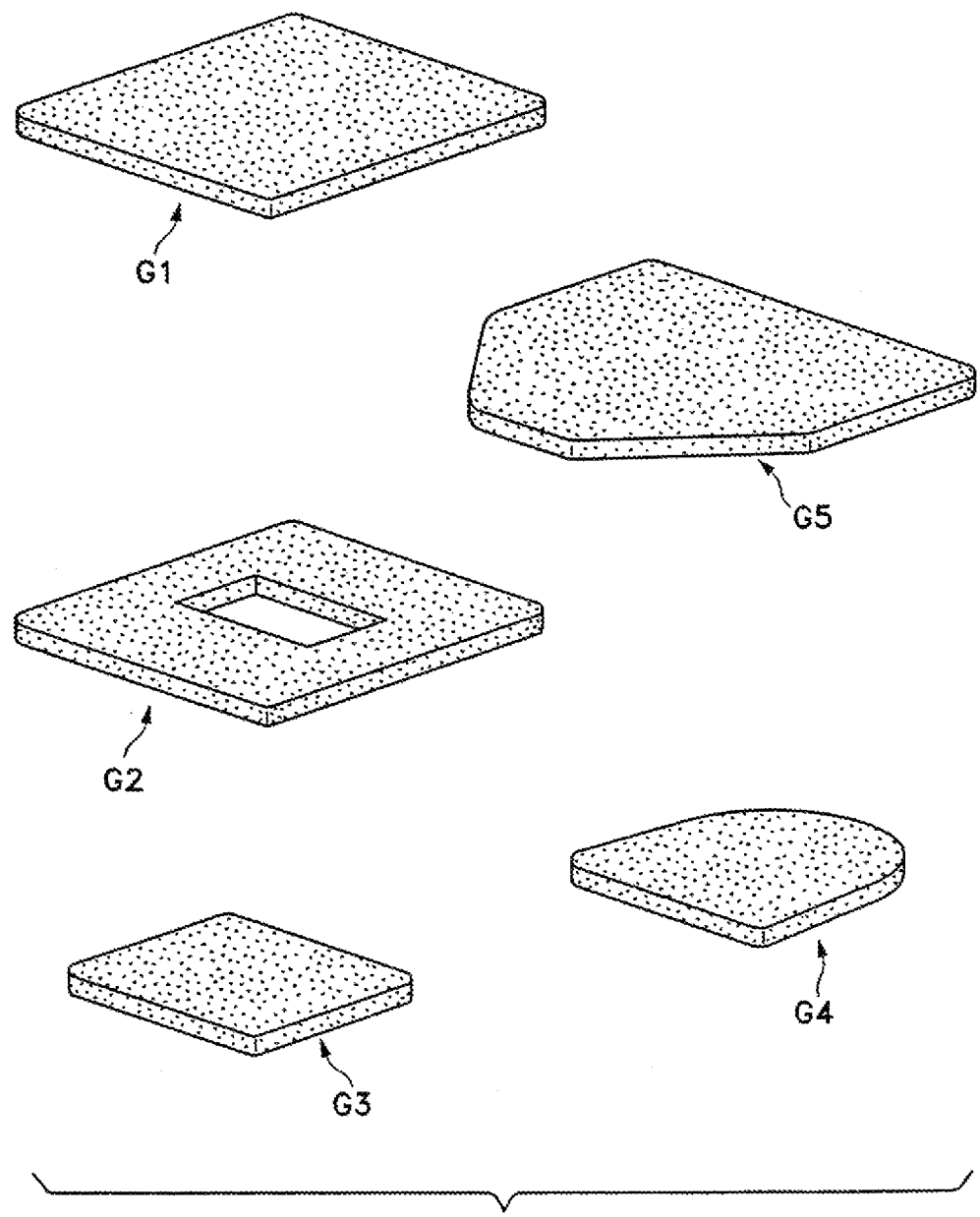
FIG. 9 illustrates various pad configurations and geometries according to the present invention depending on the type of compression paddle or x-ray unit used in a given procedure.

Typical geometries of the present invention are illustrated in FIG. 9, including pad elements for x-ray plate 15 (G1), pad elements with windows for stereotactic use (G2), spot compression paddles (G3), coned compression paddles (G4), and axillary paddles (G5).

It is noted that while these configurations reflect the geometries of various commercially available compression paddles and x-ray cassette holders, the present invention may be manufactured in a wide array of sizes and shapes. The present invention includes pad assemblies, where the pad elements are modular (e.g., using more than one pad to cover a desired surface), or cut to fit the desired surface (oversized with an overlay pattern to guide the operator in cutting the pad to fit).

Figure 10A:
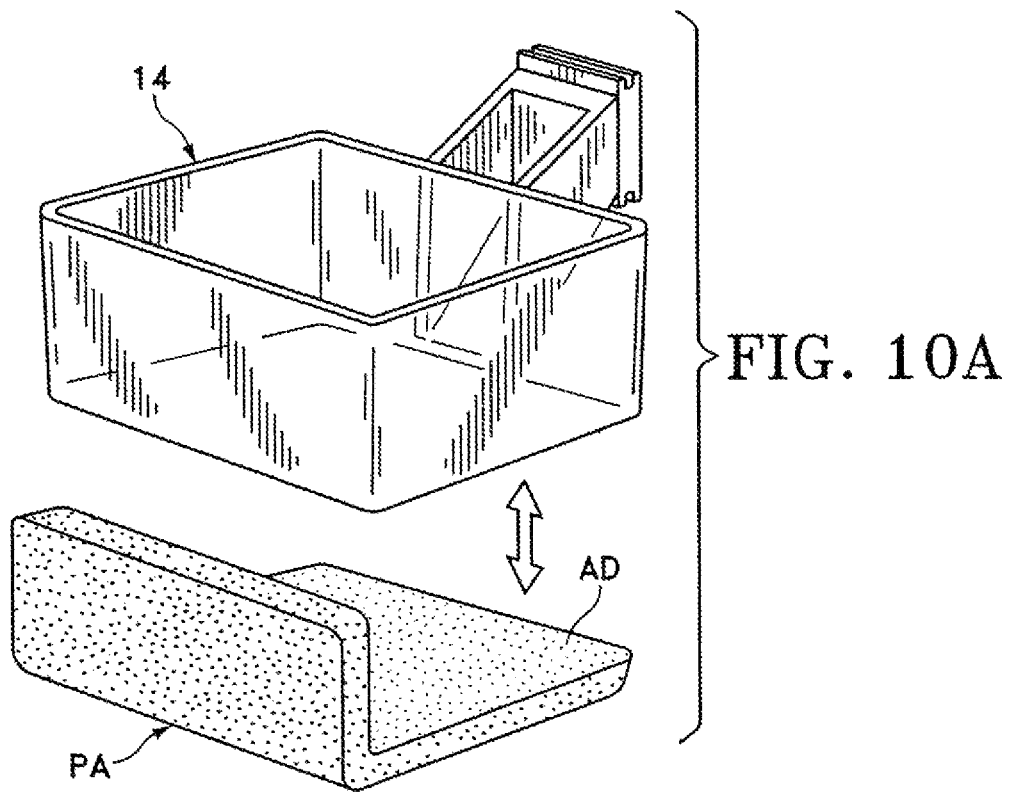
FIG. 10A illustrates an alternative embodiment of the present invention, showing the use of a self-skinned foam fastened to a compression paddle intended for use on multiple patients.
Figure 10B:
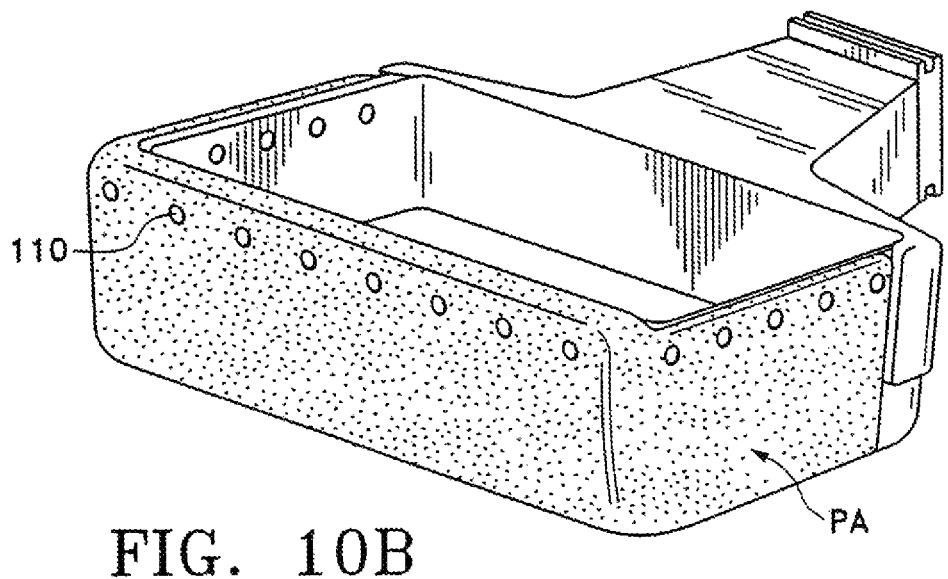
FIGS. 10B-10C further illustrate an alternative embodiment of the present invention wherein the pad of and compression paddle are integral as one unit.
Figure 10C:
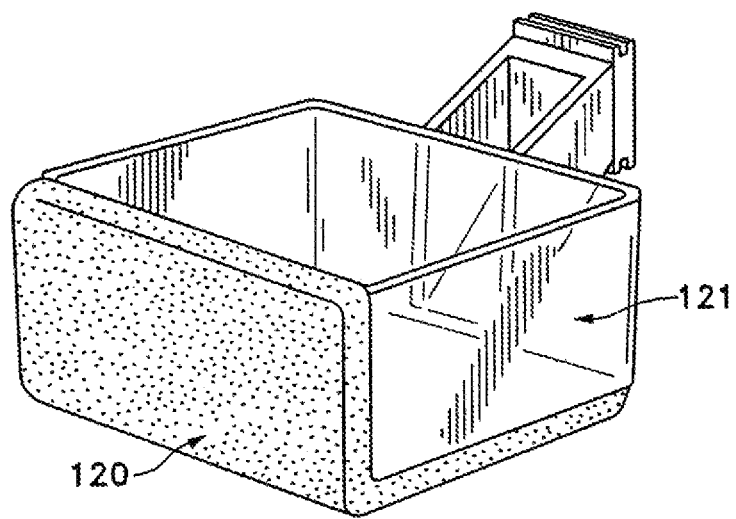

An alternative embodiment of the present invention is illustrated in FIGS. 10A-10C. FIG. 10A shows a modular configuration of the present invention wherein the pad assembly is constructed from a self skinned foam (PA), i.e., foam having an impermeable membrane covering, such as a vinyl, deployed over a frame (not shown) and fastened to a compression paddle by suction cups, magnets rivets or adhesive (AD) on the non-functional surface of the compression paddle or x-ray plate. The self-skinned configuration of the pad assembly allows for washing or disinfecting and can therefore be applied for multiple patients. FIG. 10B illustrates a pad assembly (PA) attached to the paddle on the non-functional surface by snaps or rivets 110.

FIG. 10C further illustrates an alternative embodiment of the present invention wherein the pad 120 of and compression paddle 121 are a single integral unit.

Figure 11:
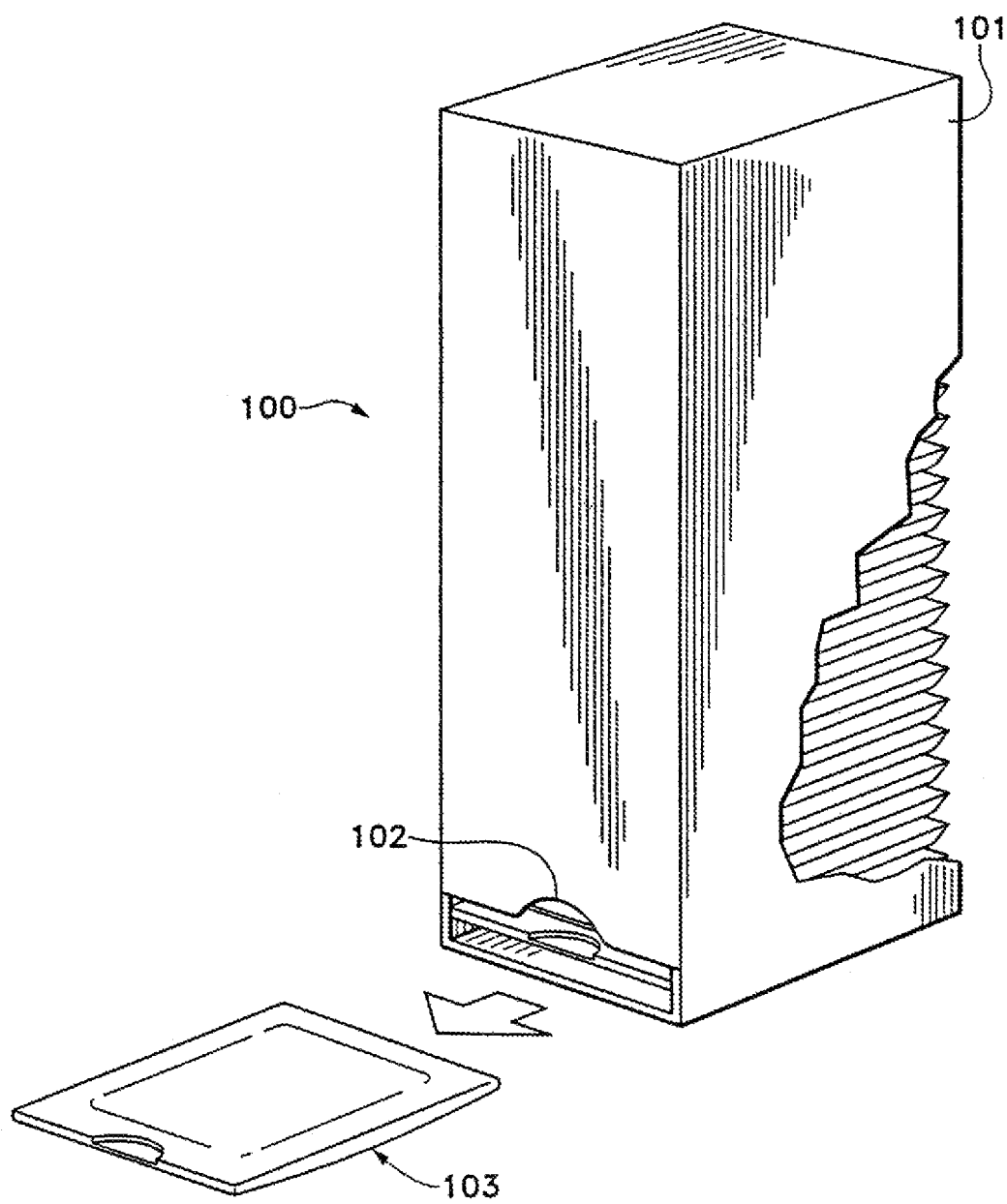
FIG. 11 illustrates a further feature of the present invention, namely a dispensing unit for storing and dispensing the disposable pads of the present invention to promote ease of use and efficiency.

FIG. 11 illustrates a dispensing unit according to the present invention for housing and dispensing the inventive pad assemblies. Dispensing unit 100 includes a housing 101 allowing multiple pad assemblies 103 to be stacked for compact storage, and an access slot 102 for allowing the user to access one pad assembly at a time.

While the above is a complete description of the preferred embodiments of the invention, various alternatives, modifications, and equivalents may be used. Therefore, the above description should not be taken as limiting the scope of the present invention.

What is claimed is:

1. A device for attachment to a compression surface of a compression device of a mammography unit, the device comprising:
    a radiolucent material having a first surface and a second surface, at least a portion producing no significant visual artifact on a mammogram while in use; and
    an attachment element coupled to at least a portion of at least one surface of the radiolucent material for releasably attaching the first surface of the radiolucent material to the compression surface.

2. The device of claim 1, wherein the attachment element comprises an adhesive layer on at least the first surface of the radiolucent material.

3. The device of claim 2, wherein the adhesive layer covers only certain regions of the first surface.

4. The device of claim 3, further comprising wherein the adhesive layer extends along a border of the first surface.

5. The device of claim 1, wherein the compression device comprises a front surface, and wherein the radiolucent material is foldable to releasably attach the radiolucent material to the compression surface and the front surface of the compression device.

6. A device for attachment to a compression surface of a compression device of a mammography unit, the device comprising:
    a radiolucent material having a first surface and a second surface, at least a portion producing no significant visual artifact on a mammogram while in use; and
    an adhesive element coupled to at least a portion of at least one surface of the radiolucent material for releasably attaching the first surface of the radiolucent material to the compression surface.

7. The device of claim 6, wherein the adhesive element covers only certain regions of the first surface.

8. The device of claim 7, further comprising wherein the adhesive element extends along a border of the first surface.

9. The device of claim 6, wherein the compression device comprises a front surface, and wherein the radiolucent material is foldable to releasably attach the radiolucent material to the compression surface and the front surface of the compression device.

10. A method for imaging a breast using an upright imaging device comprising an x-ray source and first and second compression plates, the method comprising:
    providing a radiolucent material on a compression surface of the first compression plate in an imaging field of the x-ray source;
    compressing a breast between the first and second compression plates, the radiolucent material providing comfort during compression;
    obtaining an x-ray image of the compressed breast, the radiolucent material producing no significant visual artifact on the x-ray image; and
    removing the radiolucent material from the first compression plate after obtaining the x-ray image.

11. The method of claim 10, wherein providing the radiolucent material comprises releasably attaching the radiolucent material to the compression surface of the first compression plate.

12. A device for attachment to a compression surface of a compression device of an imaging unit, comprising:
    a radiolucent gel pad having a first surface and a second surface, the gel pad producing no significant visual artifact on an x-ray image while in use.

13. The device of claim 12, further comprising means for releasably attaching the first surface of the gel pad to the compression surface.

14. An imaging system, comprising:
    a vertically oriented base;
    an x-ray source on the base;

a first compression device comprising a first patient contact surface;

a second compression device comprising a second patient contact surface; and a radiolucent cushioning element on the first patient contact surface.

15. The imaging system of claim 14, wherein the cushioning element comprises gel material.

16. The imaging system of claim 14, wherein the first patient contact surface comprises a front surface of the first compression device.

17. The imaging system of claim 14, wherein the first patient contact surface comprises a compression surface of the first compression device within an x-ray field of the x-ray source.

18. The imaging system of claim 14, wherein the first compression device comprises a compression paddle.

19. The imaging system of claim 18, further comprising an interchange assembly for removably attaching the compression paddle to the base.

20. The imaging system of claim 14, wherein the first and second compression devices are movable relative to the base for compressing a breast to obtain a mammogram of the breast, the cushioning element configured to deform under forces applied during compression to provide comfort and produce no significant visual artifact on the mammogram.

* * * * *